(12) United States Patent
Carman et al.

(10) Patent No.: US 6,334,979 B1
(45) Date of Patent: Jan. 1, 2002

(54) GASEOUS BLEND OF $O_x$ AND ITS USE FOR BIOLOGICAL BURDEN REDUCTION

(75) Inventors: Gary B. Carman, Reno; Stephen K. Wirtz, Sparks, both of NV (US)

(73) Assignee: Cosmed Group, Inc., Coventry, RI (US)

( * ) Notice: Subject to any disclaimer, the term of this patent is extended or adjusted under 35 U.S.C. 154(b) by 0 days.

(21) Appl. No.: 09/689,631

(22) Filed: Oct. 13, 2000

Related U.S. Application Data

(63) Continuation-in-part of application No. 09/217,581, filed on Dec. 22, 1998.
(60) Provisional application No. 60/068,668, filed on Dec. 23, 1997.

(51) Int. Cl.[7] .................................................. A01N 1/00
(52) U.S. Cl. ............................ 422/33; 422/22; 422/23; 422/26; 422/27; 422/28; 422/29; 422/33
(58) Field of Search ............................... 422/22, 23, 26, 422/27, 28, 29, 33

(56) References Cited

U.S. PATENT DOCUMENTS

| | | | | |
|---|---|---|---|---|
| 3,068,064 A | | 12/1962 | McDonald | 21/58 |
| 3,549,528 A | | 12/1970 | Armstrong | 210/60 |
| 3,719,017 A | | 3/1973 | Shapiro et al. | 53/21 |
| 3,897,210 A | | 7/1975 | Gruber et al. | 21/58 |
| 3,992,147 A | | 11/1976 | Christian | 21/58 |
| 4,182,663 A | | 1/1980 | Vaseen | 204/157.1 |
| 4,200,656 A | | 4/1980 | Cohen et al. | 426/331 |
| 4,207,286 A | * | 6/1980 | Gut Boucher | 422/22 |
| 4,321,263 A | | 3/1982 | Powell et al. | 424/195 |
| 4,459,280 A | | 7/1984 | Colliopoulos et al. | 424/35 |
| 4,517,159 A | | 5/1985 | Karlson | 422/20 |
| 4,548,806 A | | 10/1985 | Colliopoulos et al. | 424/35 |
| 4,551,331 A | | 11/1985 | Rudin | 424/195.1 |
| 4,640,782 A | | 2/1987 | Burleson | 210/748 |
| 4,780,277 A | * | 10/1988 | Tanaka et al. | 422/22 |
| 4,822,563 A | | 4/1989 | Joslyn | 422/31 |
| 4,828,842 A | | 5/1989 | Furst et al. | 424/480 |
| 4,889,708 A | | 12/1989 | Latif et al. | 424/43 |
| 4,988,484 A | | 1/1991 | Karlson | 422/186.19 |
| 4,989,363 A | | 2/1991 | Doernemann | 43/124 |
| 4,998,377 A | | 3/1991 | Tsutsumi et al. | 43/125 |
| 5,069,880 A | | 12/1991 | Karlson | 422/186.19 |
| 5,120,512 A | | 6/1992 | Masuda | 422/297 |
| 5,135,721 A | | 8/1992 | Richard | 422/111 |
| 5,178,896 A | | 1/1993 | Langner | 426/590 |
| 5,200,158 A | | 4/1993 | Jacob | 422/292 |
| 5,219,570 A | | 6/1993 | Barbera et al. | 424/195.1 |
| 5,229,117 A | | 7/1993 | Leland et al. | 424/195.1 |
| 5,241,803 A | | 9/1993 | Griffin | 53/425 |
| 5,344,622 A | | 9/1994 | Faddis et al. | 422/306 |
| 5,413,758 A | * | 5/1995 | Caputo et al. | 422/22 |
| 5,518,698 A | | 5/1996 | Karlson | 422/186.18 |
| 5,678,352 A | | 10/1997 | Leitner et al. | 43/125 |
| 5,702,669 A | | 12/1997 | Green | 422/30 |
| 5,897,841 A | | 4/1999 | Shroff | 422/129 |
| 6,027,667 A | | 2/2000 | Horn Feja et al. | 252/372 |

FOREIGN PATENT DOCUMENTS

JP          48011364 A   *   2/1973

OTHER PUBLICATIONS

Article: "Ozone Sterilization"; E. Karlson, D.Sc.; Jul., 1997; pp. 43–45.

* cited by examiner

Primary Examiner—Robert J. Warden, Sr.
Assistant Examiner—Imad Soubra
(74) Attorney, Agent, or Firm—Piper Marbury Rudnick & Wolfe LLP; Laura D. Donnelly

(57) ABSTRACT

A gaseous blend of $O_x$ and a method for significantly reducing the biological load on consumer products such as food products, botanicals and cosmetic ingredients is disclosed. The gaseous blend of $O_x$ consists at least in part of $O_3$. The method involves applying a continuous stream of oxygen-containing, i. e., $O_x$, gas to a material at a predetermined temperature, pressure and relative humidity. The continuous stream of $O_x$ gas is prepared in an $O_x$ generation cell, which contains a means for generating the $O_x$ gas at a pressure less than 20 lbs/in$^2$ using, for example, one or more of the following: corona discharge, high frequency electrical discharge, ultraviolet light, x-ray, radioactive isotope and electric beam.

12 Claims, 3 Drawing Sheets

GASEOUS BLEND OF $O_x$ AND ITS USE FOR BIOLOGICAL BURDEN REDUCTION

This application is a Continuation-in-part of U.S. application Ser. No. 09/217,581, filed Dec. 22, 1998, which is a regular national application claiming priority from provisional application Ser. No. 60/068,668, filed Dec. 23, 1997. The entirety of both are incorporated herein by reference.

BACKGROUND OF THE INVENTION

FIELD OF THE INVENTION

The present invention generally relates to a gaseous blend of $O_x$, and a method for applying the gaseous blend of $O_x$, that can be utilized to significantly reduce the biological load on consumer products such as food products, botanicals and cosmetic ingredients, which have traditionally been treated with commercial sterilants or fumigants such as ethylene oxide, propylene oxide, methyl bromide, hydrogen phosphide, steam (heat), irradiation, and the like.

BACKGROUND OF THE TECHNOLOGY

A number of commercial fumigants are presently used to treat foodstuffs and other stored commodities. The most widely used fumigants are methyl bromide, hydrogen phosphide, and hydrogen cyanide. As disclosed in U.S. application Ser. No. 09/217,581, many of these compounds pose hazardous conditions for application personnel and can form deleterious residues in the foodstuffs and commodities that are treated. Furthermore, some of the traditional fumigants have been identified with the formation of carcinogens and mutagens which thus limit the products that can be treated.

U.S. Pat. Nos. 5,897,841 and 6,027,667 disclose the use of $CO_2$ as a carrier gas for phosphine fumigant.

U.S. Pat. No. 4,889,708 discloses a mixture of phosphine and $CO_2$ and the use thereof to fumigate stored produce, such as grains and other commodities.

U.S. Pat. No. 4,200,656 discloses the use of $CO_2$ as a carrier for methyl bromide in fumigation.

U.S. Pat. No. 4,998,377 discloses the use of $CO_2$ as a carrier for methyl bromide and hydrogen phosphide in fumigation.

U.S. Pat. No. 5,678,352 discloses the use of $CO_2$ as a carrier for toxic agents such as methyl bromide during fumigation.

U.S. Pat. No. 4,989,3 63 discloses application of $CO_2$ in pesticidal quantities for fumigation. The process disclosed in U.S. Pat. No. 4,989,363 require administration of the $CO_2$ for a period of time of at least about 5 days.

Other procedures that have been developed to treat products utilize heat, ionizing radiation, and other chemical compounds. All of these procedures are potentially detrimental to the products' nutritional, physical and/or chemical attributes and thus make them undesirable. Insects and other pests damage to food products and other commodities account for billions of dollars of losses in the United States annually. Traditionally, a number of fumigants have been utilized to control these pests by their application under air tight tarpaulins, in sealed rooms and in steel chambers. All three primary gaseous fumigants; i.e., methyl bromide, hydrogen phosphide and hydrogen cyanide, are facing major regulatory restrictions and/or total phase out agreements over the next few years. With these limitations in mind, the search for effective alternatives has evolved the use of materials such as methyl iodide and sulfonyl fluoride. Unfortunately, these alternatives have limitations due to factors such as worker exposure, halogen content and damage to certain commodities.

Ozone ($O_3$) and its primary active component, atomic oxygen, have been used in water and commodity sterilization for about 100 years. However, as discussed in more detail below, prior treatment methods using $O_3$ would be ineffective for many applications.

U.S. application Ser. No. 09/217,581 discloses a method and apparatus that uses a gaseous mixture of oxygen-containing gases, i.e., $O_3$, $O_2$ and $O_1$, hereinafter referred to as $O_x$, to reduce biological loads on consumer products to eliminate pathogens while maintaining product stability.

As an advancement to the invention disclosed in application Ser. No. 09/217,581, the present inventors have surprisingly discovered that for a number of consumer products, $O_x$ biological burden reduction is even more effective at two distinct temperature ranges. With the appropriate adjustments to other parameters, both temperature ranges can be used for enhanced microbiological reduction and insect control, The present inventors have thus discovered that $O_x$'s effectiveness as a fumigant can be maintained and in some cases enhanced while increasing the treatment temperature. When the temperature is increased, certain other $O_x$ treatment parameters must also be adjusted away from those originally used for microbiological reduction.

SUMMARY OF THE INVENTION

It is desirable to treat a wide variety of consumer products in a cost effective manner. The gaseous blend of $O_x$, and method of the present invention permit fumigation (hereinafter referred to as "biological burden reduction" of a product in its original container (e.g., burlap bag, fiber drum, kraft paper bag, plastic bag, etc.)). Thus, double handling, product loss, and post treatment contamination are reduced.

The gaseous blend of the present invention consists at least in part of $O_3$.

The method of the present invention utilizes the gaseous blend of $O_x$ in a technologically advanced treatment system that overcomes the limitations formerly encountered with $O_3$ treatment on biological burden. Prior $O_3$ treatmnents include, for example, (1) the submersion of an article to be treated in ozone-containing water and the bubbling of ozonated water over the article (see, e.g., U.S. Pat. No. 4,517,159 to Karlson and U.S. Pat. No. 4,640,872 to Burleson); and (2) the static treatment of medical devices and food products with gaseous ozone (see, e.g., U.S. Pat. No. 3,179,017 to Shapiro et al., U.S. Pat. No. 5,069,880 to Karlson, and U.S. Pat. No. 5,120,512 to Masuda.) Systems utilizing such as described above have encountered several limitations. The incorporation of ozone gas into water and then submersion of items(s) to be sterilized or the spraying of ozone treated water onto the surface of item(s) to be sterilized limit the process to products that can be soaked in water. The few gaseous uses of ozone have been limited to the surface treatment of medical devices and the like due to the lack of adequate penetration into compacted products. Thus, although these past processes have proven the efficacy of ozone as a sterilant, the limitation of the use of ozone as a surface treatment has not presented ozone as a reliable sterilant or fumigant for products contained within commercial containers.

In addition to the generation of the ozone molecule, the present invention also utilizes the quenching effect of other inert gases to assist ozone generation, thereby increasing the stability of the $O_x$ radicals. Argon and carbon dioxide ($CO_2$) can be used in the method of the present invention to achieve these factors. Furthermore, the presence of atmospheric nitrogen has been utilized in the food industry for many years to protect sensitive oils and fats from oxidative rancidity. Small quantities of nitrogen can be used in the method of the present invention to assist in the protection of sensitive food components as well as assisting in the stabilization of the $O_x$ generation.

Accordingly, it is an object of the present invention to provide a gaseous blend of $O_x$ and a method for applying the gaseous blend of $O_x$ for reducing biological burden from consumer products.

It is another object of the present invention to provide a gaseous blend of $O_x$ and method for applying the gaseous blend of $O_x$ for reducing biological burden from consumer products in a safe manner.

It is thus an object of the present invention to eliminate the health risks that are associated with the reduction of biological burden from consumer products.

It is a further object of the present invention to provide a simple, efficient and economical gaseous blend of $O_x$ and a method for applying the gaseous blend of $O_x$ for reducing biological burden from consumer products that can be used at the site of production and/or packaging of such products.

In accordance with the above and other objects, the inventive gaseous blend consists of at least $O_3$. The inventive method for applying the gaseous blend comprises applying a continuous stream of $O_x$ gas to a material at a specified temperature. The first temperature range is 45° F. to 60° F. The second temperature range is 90° F. to 130° F. In conjunction with temperature, adjustments to other parameters proves beneficial depending on the commodity being treated and organism being targeted. With the eventual elimination of methyl bromide as a fumigant, development of alternative treatment methods has become very important. The present inventors have discovered that $O_x$'s effectiveness as a fumigant can be maintained and in some cases enhanced while increasing the treatment temperature. When the temperature is increased, certain other $O_x$ treatment parameters must also be adjusted away from those originally used in application Ser. No. 09/217,581 for microbiological reduction.

The continuous stream of $O_x$ gas is prepared in an $O_x$ generation cell, which contains a means for generating the $O_x$ gas at a pressure less than about 20 lbs/in$^2$, for example, one or more of the following: corona discharge, high frequency electrical discharge, ultraviolet light, x-ray, radioactive isotope and electron beam.

As discussed herein, $N_2$, $CO_2$ and/or Ar may be added during $O_x$ treatment. The addition of 0%–70% $N_2$, 20%–100% $CO_2$ and/or 1%–18% Ar increases the generation of an $O_x$ quenching effect. Penetration of $O_x$ into the material being treated is thus enhanced. In addition, argon is unique among the (inert) Noble Gases, in that it is soluble in both water and organic liquids. (The Merck Index Eleventh Edition). This characteristic theoretically enables argon to become a glue of sorts. Argon is capable of attaching to gases without reacting thereto. Argon thus assists in $O_x$ quenching by attaching to the $O_x$ molecules and preventing the $O_x$ molecules from colliding into each other. Argon also loosely binds hydrophilic and hydrophobic materials, thus allowing one to be diffused through the other, without reacting with either. This characteristic is useful in accelerating the diffusion of $O_x$ into and through hydrophilic materials such as fats, oils and cell walls.

An apparatus such as that disclosed in application Ser. No. 09/217,581, may be used to carry out the method of the invention.

The apparatus disclosed in application Ser. No. 09/217,581 comprises:

(a) a biological burden reduction chamber;

(b) a vacuum pump coupled to the biological burden reduction chamber;

(c) an $O_x$ generation cell, wherein the $O_x$ generation cell contains a means for generating $O_x$ at pressure less than about 20 lbs./in$^2$ using, for example, one or more of the following: corona discharge, high frequency electrical discharge, ultraviolet light, x-ray, radioactive isotope and electron beam;

(d) a first control valve coupled to the biological burden reduction chamber and the $O_x$ generation cell, wherein the first control valve is capable of permitting $O_x$ to be drawn from the $O_x$ generation cell into the biological burden reduction chamber; and (e) a second control valve coupled to the biological burden reduction chamber, wherein the second control valve is capable of withdrawing $O_x$ contained within the biological burden reduction chamber out of the biological burden reduction chamber.

Water vapor may be introduced to the gaseous $O_x$ to maintain an appropriate humidity level, i.e., between about 20% and 98% relative humidity, and, more preferably between about 40% and 75% relative humidity. The appropriate humidity level is dependent upon the ambient humidity and upon the product being treated. For example, granular and powered products require a relatively low humidity level to prevent growth of mold and yeast thereon. However, depending on the length of treatment time, any vacuum that may be created during the process removes humidity, thus requiring the addition of humidity. The $O_x$ gas may then be passed through a commercially available catalytic destruct unit to eliminate any residual $O_3$ and $O_1$ before the gas stream is discharged to the atmosphere.

The present invention is also directed to treated consumer products that result from use of the present inventive gaseous blend of $O_x$ and method.

Additional objects and attendant advantages of the present invention will be set forth in the description and examples that follow, or may be learned from using the gaseous blend or practicing the method of the present invention. These and other objects and advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further objects and attendant advantages, will best be understood by reference to the following detailed description, taken in conjunction with the accompanying drawings.

BRIEF DESCRIPTION OF THE DRAWINGS

In the following description, like parts are designated by like reference numerals throughout the figures.

DESCRIPTION OF PREFERRED EMBODIMENTS

Figure 1:
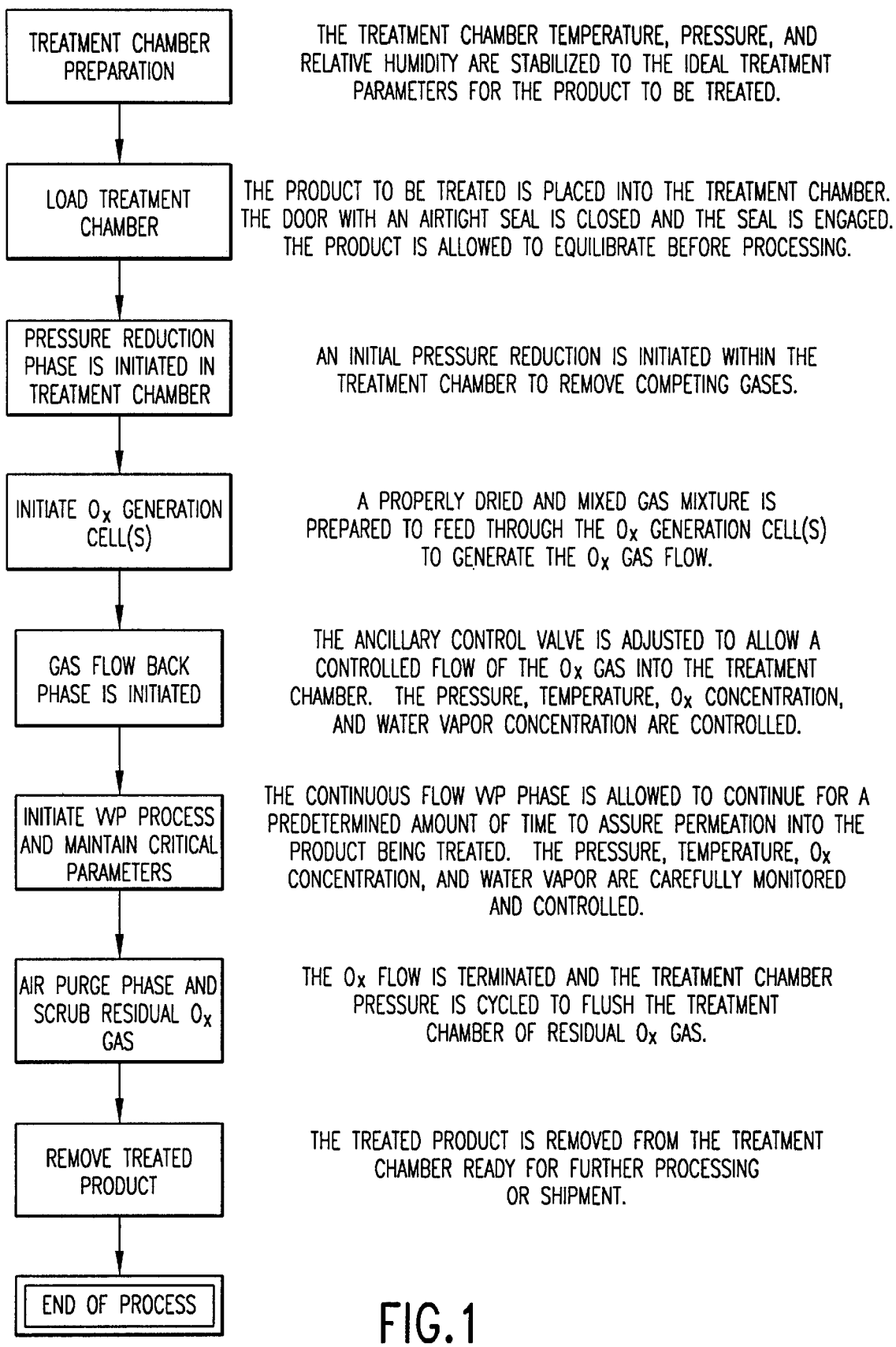
FIG. 1 is a flow chart showing an embodiment of a method for using a continuous flow of $O_x$ to reduce biological burden in accordance with the method of the present invention.

All patents, patent applications and literatures that may be cited herein are incorporated herein by reference.

The antibacterial potential of $O_3$ has been recognized for many years. $O_3$ is widely used as a disinfectant for sewage treatment and for purification of drinking water. It has, however, failed to gain acceptance as a biological burden reduction treatment for consumer goods. The primary reason for this failure is that the $O_3$ molecule is highly unstable and quickly reverts to $O_2$ if it does not encounter a susceptible substrate with which to react. $O_3$ also has the capacity to react with a broad array of substrates and would be expected to react with packaging materials surrounding the items being sterilized. This further reduces the number of $O_3$ molecules available to react with and inactivate microbial contaminants.

Previous attempts to use $O_3$ as a biological burden reduction treatment include the reliance upon filling a sterilization chamber with $O_3$ and exposing the materials to be treated in static fashion for various periods of time without replenishment of $O_3$ See for example, U.S. Pat. Nos. 3,719,017 and 5,069,880. Under these conditions, the concentration of $O_3$ within the chamber would be expected to rapidly decrease to a level below that required for effective biological burden reduction due to the short half life of $O_3$, which is typically less than 20 minutes. A further disadvantage of the static exposure technology is the reliance on simple diffusion to promote permeation of the $O_3$ molecules through packaging materials and into interstices of the materials being treated. Thus, such methods do not achieve adequate permeation into the material being treated.

The present invention, which has been designated "dynamic $O_x$ biological burden reduction," offers significant advances over the prior static biological burden reduction technology in that it provides a continuous flow of $O_x$, i.e., between about 0.03% and 16%, throughout the treatment cycle and promotes rapid permeation of $O_x$ through packaging materials and into the voids and interstices of the materials undergoing treatment. Continuous operation of the vacuum pump and $O_x$ generator during biological burden reduction ensures that the concentration of $O_x$ remains essentially the same throughout the process by constantly supplying newly generated $O_x$ molecules to replace those molecules which have spontaneously degraded to inactive $O_2$ and those which have reacted during the process.

Dynamic $O_x$ biological burden reduction provides significant cost advantages over existing biological burden reduction technology. The most significant savings derive from the fact that the $O_x$ biological burden reducing gas may be generated on site, during the process.

Because $O_x$ is not flammable or explosive, facilities need not include damage-limiting construction or explosion-proof equipment. Another advantage of dynamic $O_x$ biological burden reduction is that scrubbing will be easily accomplished using existing technology. Moreover, $O_3$ is classified by the U.S. Food and Drug Administration as a generally recognized as safe "GRAS" substance.

The dynamic $O_x$ biological burden reduction process of the invention has proven successful in the treatment of a wide variety of materials, including spices, flavorings, and packaging materials.

Figure 3:
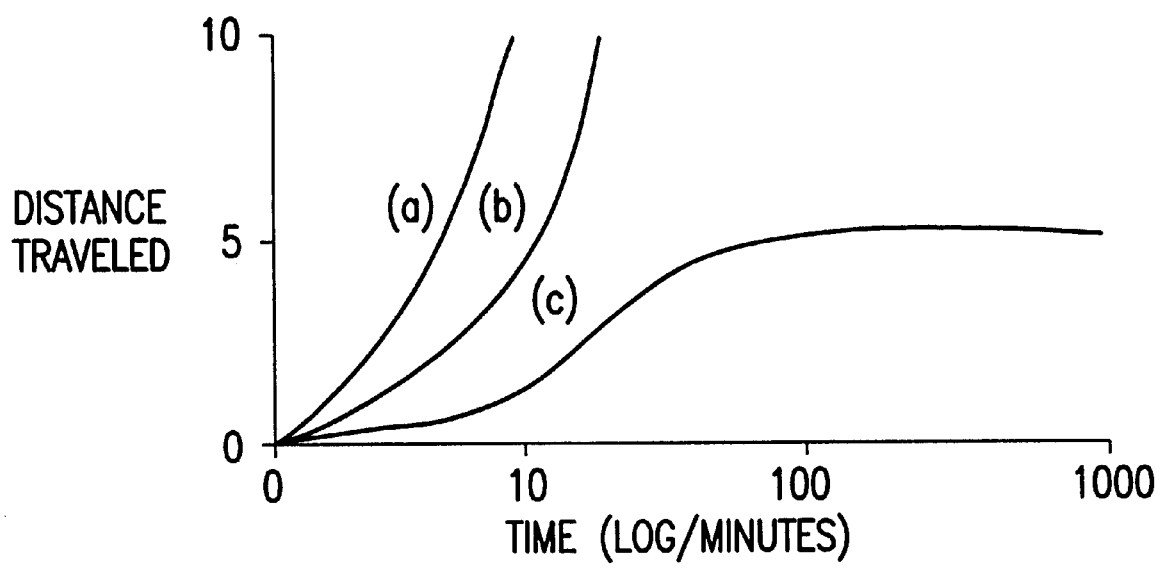
FIG. 3 is a graph comparing permeation of $O_x$ gas for (a) VVP+$CO_2$, +$O_x$ in accordance with an embodiment of the method of the invention, (b) VVP+$O_x$ in accordance with an embodiment of the method the invention, and (c) static+$O_x$ in accordance with conventional use of gaseous $O_x$ in a static fashion.

Referring to FIG. 3, which is a graph comparing permeation $O_x$ gas for (a) VVP+$CO_2$+$O_x$ in accordance with an embodiment of the method of the invention, (b) VVP+$O_x$ in accordance with an embodiment of the method the invention and (c) static+$O_x$ in accordance with conventional use of gaseous $O_x$ in a static fashion. The static flow of gas (c) demonstrated a limited permeation, which quickly stopped altogether. The (VVP) process (a) and (b), on the other hand, demonstrated a continuous progression through the packed column; completely depleting the chemical indicator. This embodiment enhances the permeability of $O_x$ gases into commercially sized containers of granular and powdered food components. The observation of treatment in accordance with the invention to live insects and microbiological and chemical indicators has been utilized to measure the incorporation of lethal doses of $O_x$ into these containers. Via comparative data (see FIG. 3), a static flow of $O_x$ bearing gas (curve (c)) has proven ineffective in driving the $O_x$ into the containers. This embodiment utilizes a process herein described as the Vacuum Vapor Phase Dynamic Flow (VVP). In theory, and supported by empirical data, VVP acts as the driving force to enhance permeation of the $O_x$ gases by two factors. The first factor is the molecular acceleration of the $O_x$ gases due to the flashing of the concentrated $O_x$ gas into the reduced pressure treatment chamber. This creates a driving force at a molecular level that continuously forces the $O_x$ gases into the product being treated. The second factor is the resulting reduction of molecules within the reduced pressure treatment chamber which reduces the incidence of molecular collision of the $O_x$ gases. Molecular collision of the $O_x$ gases causes rapid degradation of the $O_3$ and $O_1$ radicals present therein, thereby reducing the gases effectiveness. Without the VVP process, the $O_x$ gas flow could only be utilized as a surface treatment of non-amorphous materials, therefore, the VVP process expands the capabilities of the present invention to process virtually any type of product in-situ, thus eliminating the need to repackage the product after treatment.

The method of the present invention avoids many of the limitations of previous practices by avoiding the need for water sprays and/or water immersion of the substrate to be treated. Many products such as spices, flour-based products, sugar-based products, cosmetic bases, herbs, and botanicals, which are sensitive to high levels of moisture, can be treated using the method of the present invention. The method of the present invention also avoids the need to open conventional commercial packaging before treatment, thus avoiding unnecessary product degradation and loss. The product may be treated in situ utilizing conventional processing. Previous methods have required the product to be agitated, blended, bubbled, or re-packaged during or immediately upon completion of the treatment. Due to the increased permeation of the VVP process and the $O_x$ gas mixture, these damaging handling practices are avoided. The extended half life of the $O_x$ radicals allows the active portions of the treatment gas to fully penetrate the substrate and act upon offending organisms. In combination with carbon dioxide, the stabilized $O_x$ gas mixture is further enhanced by the increased respiration rates of the offending organism(s) while in the presence of the permeated $O_x$ gases.

Figure 2:
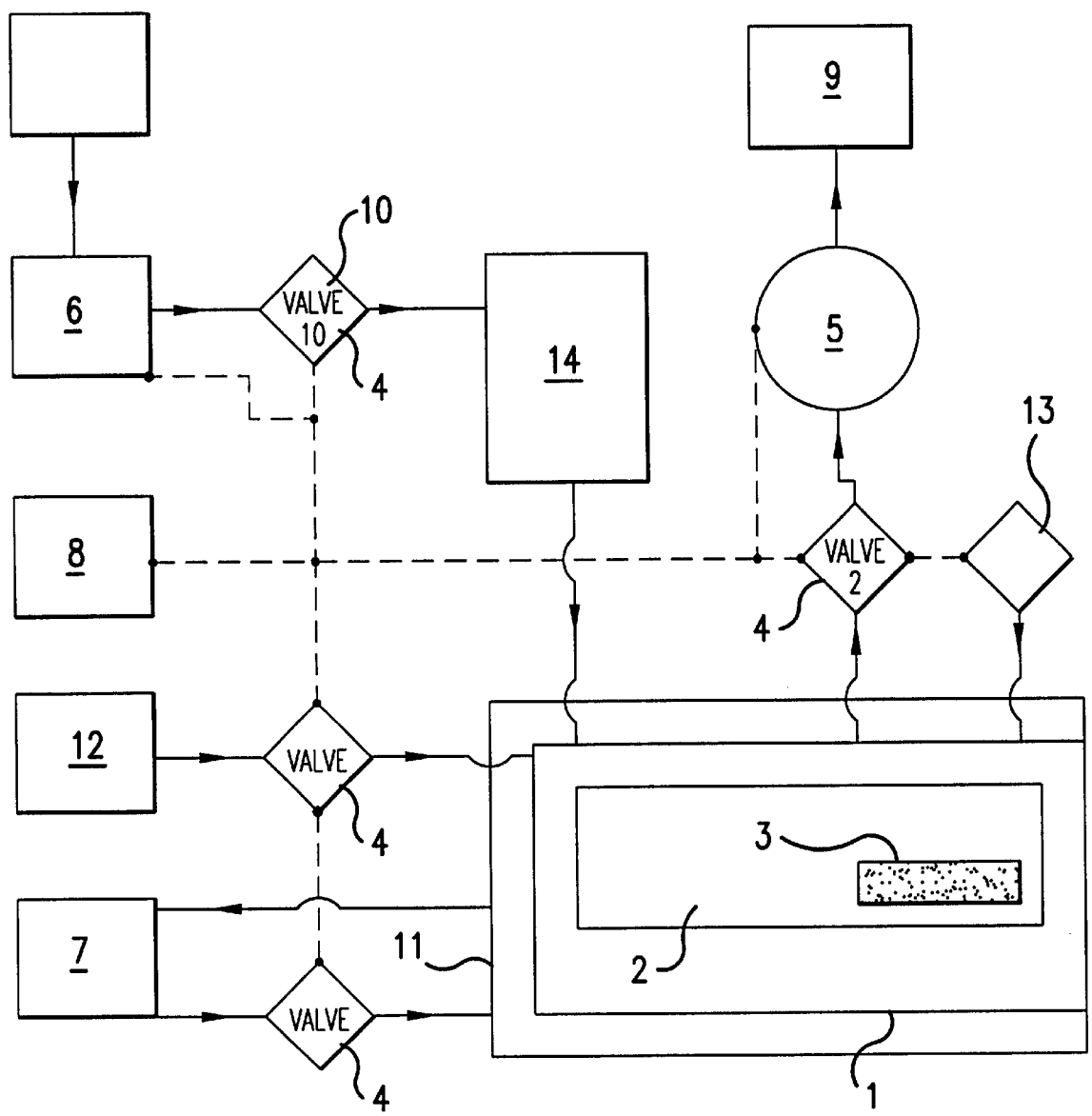
FIG. 2 is a schematic showing one example of an apparatus for using a continuous flow of $O_x$ to reduce biological burden in accordance with the method of the embodiment in FIG. 1.

Referring to FIG. 2, an apparatus that may be used to practice an embodiment of the method if the invention includes a biological burden reduction chamber 1 equipped with a gasketed door 2 that can be opened to accommodate placement of material 3 within the biological burden reduction chamber 1 and tightly closed and latched. The biological burden reduction chamber 1 permits a vacuum tight seal during the process. The chamber 1 is connected via piping and appropriate control valves 4 to a vacuum pump 5 and separately to a generator of $O_x$ 6, which, in turn is connected to a gas washer 14 and an air preparation regulated feed gas supply 15. The biological burden reduction chamber 1 is jacketed by coils of metal tubing 11 through which heated or chilled water generated by a temperature control (e.g., glycol) system 7 may be pumped to regulate the temperature within the chamber 1 during the biological burden reduction process. The entire biological burden reduction process may be controlled and monitored by a programmable industrial process controller 8. The chamber 1 is also connected to a water vapor source 12 to provide humidity control.

According to an embodiment of the invention, material 3 for which biological burden is to be reduced is placed within the biological burden reduction chamber 1 and the door 2 is closed and latched. The process is then initiated by activating the process controller 8, which has previously been programmed with the appropriate process parameters such as pressure, the specified temperature and humidity. The controller 8 first activates the vacuum pump 5 and ancillary valves 4 to reduce the biological burden reduction chamber pressure to a preset level between, e.g., 0 and 15 psia depending on the pressure sensitivity of the product being treated, to introduce via the water vapor source 12 the desired humidity, and to maintain a desired temperature via the temperature control system 7. After the appropriate vacuum level has been reached, the controller 8 initiates biological burden reduction by activating the $O_x$ generator 6 and opening a control valve 10, allowing the washed $O_x$ stream to be drawn into, through and out of the chamber 1 by the pressure differential. The vacuum pump 5 and $O_x$ generator 6 operate continuously during the process.

Exposure to the $O_x$ gas mixture may be varied in time from several minutes to several hours, depending on the material being treated. Once the biological burden reduction phase is complete, the vacuum pump 5 and $O_x$ generator 6 are inactivated and fresh air is allowed to enter the chamber 1 via the air purge valve 13. All $O_x$ gases may then be passed through a commercially available catalytic destruct unit 9 which eliminates any residual $O_3$ and $O_1$ before the gas stream is discharged to the atmosphere. The treated material 3 can then be removed from the chamber 1 and is ready for use following appropriate tests to confirm biological burden reduction.

EXAMPLES

The present invention will be further illustrated by the following non-limiting Examples.

Example 1

The method of the invention is carried out using the VVP process as described above at a specified temperature range of 90° F. to 130° F. According to this example, the following adjustments to the VVP process for fumigation are made:

| | |
|---|---|
| Vacuum Vapor Phase (VVP) | 8–10 psia for pressure sensitive commodities like fresh fruits and vegetables, such as: papayas, oranges, grapes, squash, bell peppers, and tomatoes. |

-continued

| | |
|---|---|
| | 0–6 psia for non pressure sensitive commodities like spices and dehydrated vegetables, such as: black pepper, cloves, nutmeg, diced bell peppers, minced onion and garlic. |
| Exposure Time | 0.5 to 3 hours. |
| $O_3$ concentration | 500 to 15,000 ppm. |
| Feed Gas Blend | Concentration of oxygen ($O_2$), 0 to 100%. Concentration of carbon dioxide ($CO_2$), 1–100%. No adjustment for nitrogen ($N_2$), 0–70%. No adjustment for Argon (Ar), 1–18%. |
| Temperature | 90° F. to 130° F. |
| Humidity Control | Typically on the dryer side of the same non-condensing range of 40% to 70% RH, control is less critical, due to shorter treatment times. |
| Commodity Treated | Granulated Raw Sugar |
| Target Organism | Book Mites |
| VVP | 6 psia |
| Feed Gas Blend | $O_2$ 87%    $CO_2$ 10%    $N_2$ 3% |
| $O_3$ Concentration | 10,000 ppm |
| Humidity | 40% |
| Temperature | 90° F. |
| Treatment Time | 2 Hr |
| Observation After Treatment | 100% elimination |

As can be seen from the above example, book mites, the target organism, were eliminated from granulated raw sugar by 100% in accordance with the method of the invention.

In addition to the increased applications and effectiveness seen when treating at warmer temperatures, several economical benefits for utilizing adjusted $O_x$ fumigation parameters can be achieved. These benefits stem from reducing the construction specifications for fumigation specific equipment. Chamber construction may now be from mild steel or epoxy coated mild steel as opposed to the much more expensive stainless steel. This is because lower $O_x$ concentrations are inherently less corrosive. Thus, all of the support equipment required for $O_x$ processing, i.e., the $O_x$ generator, the vacuum pump, the temperature and humidity control systems, can all be down-sized, lowering both their capital and operational costs.

Additional advantages that result from using increased treatment temperature for microbiological reduction and disinfestation include reductions in post-treatment odor, color loss and burn damage caused by condensation spotting. When treating pressure sensitive commodities like fresh fruits and several vegetables for microbiological reduction, the parameter adjustments listed above for fumigation have proven very effective.

Example 2

The method of the invention is carried out using the VVP process as described above at a specified temperature range of 90° F. to 130° F. According to this example, when using increased process temperature for microbiological reduction of nonsensitive small particle size commodities like spices, psyllium and dehydrated vegetables, the following adjustments should also be made:

| | |
|---|---|
| Vacuum Vapor Phase | No adjustment. 1 –6 psia |
| Exposure Time | No adjustment. 0.5–20 Hr. |
| $O_3$ concentration | 1500 to 6000 ppm. |
| Feed Gas Blend | No adjustment for $O_2$. 0–100%. Concentration of $CO_2$, 1–100%. No adjustment for $N_2$, 0–70%. No adjustment for Argon (Ar), 1–18%. |

-continued

| | |
|---|---|
| Temperature | 90° F. to 130° F. |
| Humidity Control | Typically on the dryer side of the same non-condensing gas range. 60%–80% RH. |
| Commodity Treated | Psyllium Husk |
| Target Organism | $1.2 \times 10^6$ Bacillus Subtilis Spores |
| VVP | 6 psia |
| Feed Gas Blend | $O_2$ 2%   $CO_2$ 95%   $N_2$ 3% |
| $O_3$ Concentration | 3,000 ppm |
| Humidity | 64% |
| Temperature | 127° F. |
| Treatment Time | 20 Hr |
| Observation After Treatment | 100% elimination |

As can be seen from the above example, bacillus subtilis spores, the target organism, were eliminated from psyllium husk by 100% in accordance with the method of the invention.

Example 3

According to another embodiment of the invention, the VVP process as described is carried out using a unique gaseous mixture comprised primarily of $CO_2$ as well as smaller concentrations of $O_3$, $O_2$ and carbon monoxide (CO). The gaseous mixture is preferably fed through an ozone generator such as described above where a gaseous blend is formed consisting of $CO_2$, $O_3$, $O_2$ and CO. This gaseous blend assists in the stabilization of the $O_3$ molecules by dampening the molecular collision of the $O_3$ molecules, which would degrade this triatomic form of oxygen back to its diatomic form, atmospheric oxygen. Several benefits have been observed by generating this gaseous blend. The first benefit is to "tame" the $O_3$ so it has a chance to penetrate into the interstitial spaces of the product being treated. In addition, the $CO_2$ acts as a non-polar solvent to assist in the penetration of the gaseous blend into the commodities. By reducing the residual oxygen levels equal to or below normal atmospheric levels, the oxidative damage to the commodity is highly reduced. The presence of high levels of $CO_2$ has been shown to enhance the effects of fumigants by promoting increased respiration in insects, thereby allowing the infusion of the fumigant into the insect spiracles and coming into direct contact with the insect's bodily fluids.

As an alternative, the $CO_2$ can be mixed into an $O_3$ rich gas flow immediately after the ozone generator to assist in the formation of the gaseous blend. According to this technique, no CO is formed since no $CO_2$ molecules are cleaved. A disadvantage of this system is the increased amount of oxygen required to produce the $O_3$ in the generator, which subsequently allows the $O_3$ to degrade at an accelerated rate.

Fumigation Parameters:

| | |
|---|---|
| Vacuum Vapor Phase | 8–10 psia for pressure sensitive commodities like fresh fruits and vegetables. 0–6 psia for non pressure sensitive commodities like spices and dehydrated vegetables. |
| Exposure Time | 0.5 to 3 hours. |
| $O_3$ concentration | 500 to 1500 ppm. |
| Feed Gas Blend | Concentration of oxygen ($O_2$), 0 to 20%. Concentration of carbon dioxide ($CO_2$), 80–100%. |
| Temperature | 45° F. to 60° F. or 90° F. to 130° F. |
| Humidity Control | 40% to 70% RH. |

-continued

| | |
|---|---|
| Commodity Treated | Fresh Whole Green Banana |
| Target Organism | Nevada Fire Ants |
| VVP | 10 psia |
| Feed Gas Blend | $O_2$ 0%   $CO_2$ 100% |
| $O_3$ Concentration | 525 ppm |
| Humidity | 40% |
| Temperature | 115° F. |
| Treatment Time | 30 min |
| Observation After Treatment | 100% elimination |

As can be seen from the above example, Nevada fire ants, the target organism, were eliminated from fresh whole green banana by 100% in accordance with the method of the invention.

Sterilization Parameters:

| | |
|---|---|
| Vacuum Vapor Phase | 8–10 psia for pressure sensitive commodities like fresh fruits and vegetables. 0–6 psia for non pressure sensitive commodities like spices and dehydrated vegetables. |
| Exposure Time | 0.5 to 20 hours. |
| $O_3$ concentration | 500 to 8000 ppm. |
| Feed Gas Blend | Concentration of oxygen ($O_2$), 0 to 20%. Concentration of carbon dioxide ($CO_2$), 80–100%. |
| Temperature | 45° F. to 60° F. or 90° F. to 130° F. |
| Humidity Control | 40% to 70% RH. |
| Commodity Treated | Fresh Whole Strawberries |
| Target Organism | E. Coli $>10^6$ |
| VVP | 10 psia |
| Feed Gas Blend | $O_2$ 2%   $CO_2$ 98% |
| $O_3$ Concentration | 1337 ppm |
| Humidity | 40% |
| Temperature | 112° F. |
| Treatment Time | 60 min |
| Observation After Treatment | Post treatment <10 |

As can be seen from the above example, E. coli, the target organism, was eliminated from fresh whole strawberries by a factor of more than $10^5$ in accordance with the method of the invention.

The gaseous blend of $O_x$ and method for applying the gaseous blend of $O_x$ of the invention are thus an excellent substitute for commercial sterilants and fumigants in all of its current uses and is also useful for the treatment of many food ingredients on which use of commercial sterilants and fumigants is not permitted, including cocoa beans, grains, and edible gums.

The gaseous blend of $O_x$ and method for applying the gaseous blend of $O_x$ of the invention have been shown to be highly insecticidal and are therefore a useful substitute for certain current uses of methyl bromide, which, as discussed herein, are soon to be banned under the direction of the Montreal Protocols of 1997.

What is claimed:

1. A method for fumigation to reduce biological burden on a material, comprising:

(a) applying a continuous stream of non-plasma $O_x$ gas to said material in a sealed biological burden reduction chamber, wherein said continuous stream of non-plasma $O_x$ gas is drawn into, through and out of said biological burden reduction chamber throughout fumigation, and wherein said $O_x$ gas includes $O_1$, $O_2$ and $O_3$; and (b) maintaining a pressure of between about 2.91 psia and about 15 psia, temperature of between about 45° F. and about 60° F. and relative humidity of about 20% to about 98% in said biological burden reduction chamber.

2. The method of claim 1, wherein said pressure is maintained at 2.91–6 psia and said relative humidity is maintained at 60–80%.

3. The method of claim 2, wherein said material is exposed to said non-plasma $O_x$ gas for 0.5 to 20 hours.

4. The method of claim 1, wherein said pressure is maintained at 2.91–10 psia and said relative humidity is maintained at 40–70%.

5. The method of claim 4, wherein said material is exposed to said non-plasma $O_x$ gas for 0.5 to 3 hours.

6. The method of claim 1, wherein said non-plasma $O_x$ gas is generated at a pressure of about 10 lbs/in$^2$ to about 20 lbs/in$^2$.

7. A non-plasma gaseous blend for fumigation, said non-plasma gaseous blend comprising $O_3$ and $CO_2$ under a pressure of between about 2.91 psia and about 15 psia.

8. The gaseous blend of claim 7, comprising 0.03 to 16% $O_3$ and 30 to 100% $CO_2$.

9. The gaseous blend of claim 7, further comprising $O_2$.

10. The gaseous blend of claim 7, further comprising CO.

11. A method for fumigation to reduce biological burden, comprising administering the gaseous blend of claim 7 to said biological burden for an amount of time sufficient to reduce said biological burden.

12. A method for fumigation to reduce biological burden on a material, comprising:
 (a) applying a continuous stream of non-plasma $O_x$ gas to said material in a sealed biological burden reduction chamber, wherein said continuous stream of non-plasma $O_x$ gas is drawn into, through and out of said biological burden reduction chamber throughout fumigation, and wherein said $O_x$ gas includes $O_1$, $O_2$ and $O_3$; and
 (b) maintaining a pressure of between about 2.91 psia and about 15 psia, temperature of between about 90° F. and about 130° F. and relative humidity of about 20% to about 98% in said biological burden reduction chamber.

* * * * *